United States Patent [19]

Cheslow

[11] 4,014,340
[45] Mar. 29, 1977

[54] TAPE CLOSURE HAVING A SLOT FOR RECEIVING A DIAPER CORNER THERETHROUGH

[75] Inventor: Ernest Cheslow, Glencoe, Ill.

[73] Assignee: Johnson & Johnson, New Brunswick, N.J.

[22] Filed: Mar. 12, 1976

[21] Appl. No.: 666,275

[52] U.S. Cl. .............................. 128/287; 128/284
[51] Int. Cl.[2] ........................................ A61F 13/16
[58] Field of Search ...... 128/287, 284, 286, 290 R, 128/290 H, 289

[56] References Cited
UNITED STATES PATENTS

| | | | |
|---|---|---|---|
| 2,898,912 | 8/1959 | Adams | 128/284 |
| 2,931,361 | 4/1960 | Sostrin | 128/284 |
| 3,874,386 | 4/1975 | Kozak | 128/287 |
| 3,921,639 | 11/1975 | Cepuritis | 128/287 |

*Primary Examiner*—Stephen C. Pellegrino

[57] ABSTRACT

A disposable diaper having a facing sheet defining a diaper inside surface and a backing sheet defining a diaper outside surface is provided with adhesive tabs at corners of the diaper along one transverse margin which can be inserted through openings at corners of the diaper along the opposite transverse margin of the diaper. The corners of the diaper having the tabs are folded over, and an adhesive-coated free end of the tab is adhered to the backing sheet to secure the diaper about an infant.

7 Claims, 7 Drawing Figures

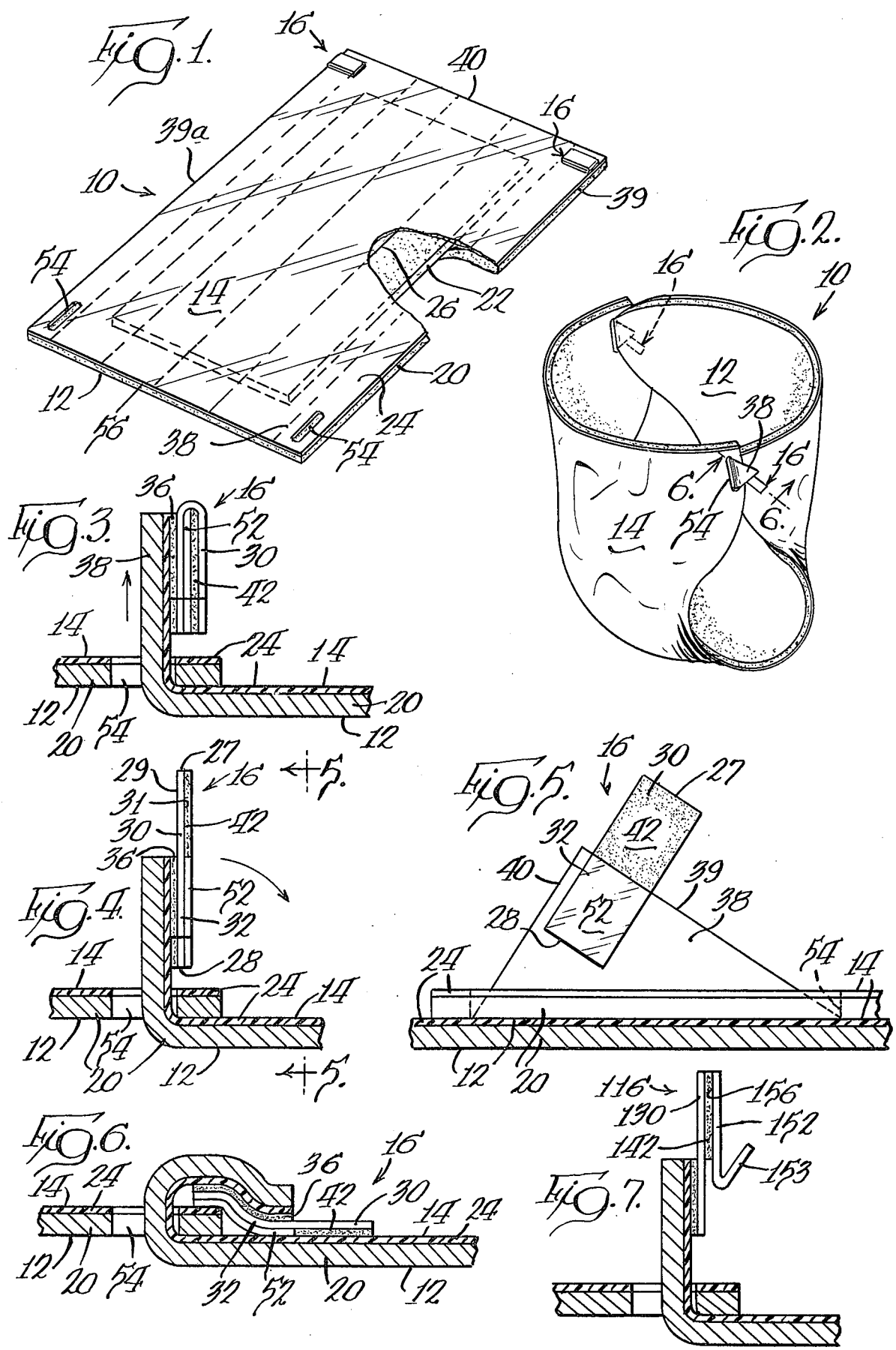

4,014,340

TAPE CLOSURE HAVING A SLOT FOR RECEIVING A DIAPER CORNER THERETHROUGH

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet therefor, generally made of a plastic film such as polyethylene film or the like. Typical disposable diaper structures are shown in U.S. Pat. No. 3,612,055 to Mesek et al. and in U.S. Pat. No. Re. 26,151 to Duncan et al.

As may be seen from the above-cited patents, it is desirable to obviate the problems that are inherent in closure systems which utilize extraneous fasteners such as safety pins, snaps and zippers. To this end, adhesive closure systems have presented acceptable solutions.

In order to protect the adhesive surfaces of the tape tabs, usually a cover strip having a release surface is applied over these adhesive surfaces for subsequent removal when the diaper is about to be used. However, such tabs usually project beyond the confines of the diaper to a considerable extent and interfere with the efficient manufacture and packaging of the diaper. Many prior art cover strips have the further disadvantage that the consumer must dispose of the cover strips when they are separated from the adhesive tabs. This is an inconvenience to the consumer who is positioning the diaper on an infant at the same time.

In an attempt to provide positive securement of the diaper on an infant, some prior art patents disclose notches or openings at one end of the diaper in which tongues from the opposite end of the diaper are receivable. For example, U.S. Pat. No. 2,890,700 to Lonberg-Holm discloses a diaper having slits at one end, with enlarged openings communicating with the slits. Tongues are provided at the opposite end of the diaper, and the tongues can be interlaced in the respective openings at the ends of the slits. It is a disadvantage of the Longberg-Holm fastening arrangement that the diaper is held on the infant only by friction, and slippage can result. Adhesive tabs are not employed, and the arrangement is not suitable for mass production at high production rates.

Likewise, U.S. Pat. No. 3,900,032 to Heurlen discloses a contoured diaper having apertures at both ends of the diaper. At each end of the diaper, the portions of the diaper between the apertures and the side margins of the diaper comprise strips. Each strip is first threaded through the adjacent aperture, pulled outwardly to twist the diaper into a hammock-like structure, and the strips are then tied to each other to secure the diaper about the infant. Adhesive tabs are not used for fastening the diaper, and the apertures facilitate in shaping the diaper in a trough-like structure rather than enhancing the securement of the diaper about the infant.

SUMMARY OF THE INVENTION

According to the present invention, tape tabs are used on each side of the diaper to secure the diaper about an infant. The diaper includes a facing sheet defining a diaper inside surface, a moisture-impervious backing sheet defining a diaper outside surface, and an absorbent panel positioned between the facing sheet and backing sheet.

Each tab comprises an elongated tape segment having a fixed end attached to a corner of the diaper along a side margin and along a transverse margin of the diaper, and a free working end having a pressure-sensitive adhesive coating on one face.

The corners of the diaper along the side margins and along the opposite transverse margin of the diaper having openings through which the free end of the tab, and the corner of the diaper to which the tab is affixed, can be inserted. The free end of the tab is then folded back and secured to the backing sheet to secure the diaper about an infant.

Both the fixed end and the free end of the adhesive tabs are secured to the diaper backing sheet where the tab is out of contact with the infant's skin. Moreover, the tape tabs remain flat against the diaper when in the folded configuration and will not interfere with the diaper manufacturing machinery and the subsequent packaging operations.

BRIEF DESCRIPTION OF THE DRAWINGS

FIG. 1 is a perspective view, partially broken away to show interior detail, of an open unfolded diaper in accordance with the present invention;

FIG. 2 is a perspective view of the diaper of FIG. 1 in a configuration assumed by the diaper when placed about an infant;

FIG. 3 is a fragmentary side elevational view of one corner of the diaper inserted through an opening at another corner of the diaper with the tab fastener in a folded position;

FIG. 4 is a fragmentary side elevational view similar to FIG. 3 but with the tab fastener in an extended position;

FIG. 5 is a fragmentary front elevational view, partially in cross-section, and taken along plane 5—5 in FIG. 4;

FIG. 6 is a fragmentary side elevational view, partially in cross-section, with the corner of the diaper having the tab fastener folded over and with the tab fastener in the working position; and FIG. 7 is a fragmentary side elevational view similar to FIG. 3 and showing an alternate embodiment of the invention.

DESCRIPTION OF THE PREFERRED EMBODIMENTS

In the following description, two digit numerals are used to refer to the embodiment illustrated in FIGS. 1–6 and three digit numerals in the one hundred series are used to refer to the embodiment illustrated in FIG. 7. The same last two digits in each numeral designate similar elements in the various embodiments.

Disposable diaper 10, illustrated in FIGS. 1 and 2, is of substantially rectangular configuration and presents inside surface 12 for direction toward an infant and outside surface 14 for direction away from the infant. Adhesive tab fastener means comprising tape segments such as tabs 16 are attached to diaper 10 for securing diaper 10 about an infant. As described in greater detail below, tabs 16 are movable from a folded-over storage position illustrated in FIG. 3 to an extended working position which is illustrated in FIG. 6.

Referring to FIGS. 1 and 3–6, diaper 10 comprises moisture-impervious facing sheet 20, defining diaper inside surface 12 and overlying moisture-retaining absorbent pad 22, and backing sheet 24 which is made of a moisture-impervious material and defines diaper outside surface 14. Absorbent pad 22 is somewhat smaller than backing sheet 24 and is centrally disposed thereon; however, absorbent pad 22 can be made coextensive with backing sheet 24, if desired. Facing sheet 20 is substantially coextensive with backing sheet 24. Both facing sheet 20 and pad 22 can be anchored to the backing sheet 24 by means of adhesive beads 26, glue spots or in any other convenient manner. For example, facing sheet 20 and pad 22 can be secured together by heat bonding.

As illustrated in FIG. 4, adhesive tab 16 has terminal edges 27 and 28, inner face 29, and outer face 31. Free working end 30 extends to outer transverse edge 27, and fixed end 32 extends from free end 30 to inner transverse edge 28. Fixed end 32 is provided with adhesive coating 36 on inner face 29 thereof for permanently attaching fixed end 32 of tab 16 to corner 38 of backing sheet 24 along a side margin 39 and transverse margin 40 of the backing sheet (FIG. 5). Adhesive coating 36 can be a pressure-sensitive adhesive composition, a heat-activated or solvent-activated composition, or the like. Free end 30 is provided with pressure-sensitive adhesive coating 42 on outer face 31 for securing the diaper about an infant.

Release means 52 is carried by tab 16 and is releasably attached to adhesive coating 42 on free end 30. Free end 30 is separable from release means 52 to make the adhesive-coated free end 30 of tab 16 available for use in securing the diaper about an infant.

Openings 54 are provided at the corners of the diaper along side margins 39 and 39a and along opposite transverse margin 56 of the backing sheet. Each opening is adapted to receive a corner of the diaper having tab 16 (FIG. 3). The tab is then unfolded from the storage position of FIG. 3 wherein adhesive coating 42 is releasably adhered to release means 52 in juxtaposition therewith, and assumes the extended position shown in FIGS. 4 and 5, whereupon the corner of the diaper having tab 16 is folded until backing sheet 24 is juxtaposed to itself and free end 30 is adhered to backing sheet 24 to secure the diaper about an infant, as shown in FIG. 6. Preferably, the corner of the diaper having tab 16 is inserted through the opening in the direction of arrow B (FIG. 3) from diaper inside surface 12 toward diaper outside surface 14, and free end 30 is folded back and is adhered to backing sheet 24 along opposite transverse margin 56.

Openings 54 preferably are oblong, perpendicular to transverse margin 40 of the backing sheet, and have a length greater than the width of tab 16. The openings may comprise slits which can be spread apart to insert tab 16 and the corner of the diaper associated with the tab through the opening. Since the openings are provided along side margins of the diaper where batt 22 does not extend, the openings extend through only facing sheet 20 and backing sheet 24.

Release means 52 may comprise a ribbon segment or release strip carried by fixed end 32 and provided with a release coated face 56 which provides the release region and faces in the same direction as diaper outside surface 14 and outer face 31 of tab 16, and an adhesive coating on opposite face 58 by means of which the release strip is anchored to outer face 31 of fixed end 32. Release means 52 may also comprise a release coating, such as a silicone release compound, or the like, on outer face 31 of fixed end 32 and which is substantially coextensive with adhesive coating 42 on free end 30 when tab 16 is folded to the storage position.

Alternatively, the outer face 31 of fixed end 32 can be suitably backsized with a release composition to provide the desired release properties for releasable attachment of adhesive coating 42 on free end 30 thereto.

Another embodiment is illustrated in FIG. 7 in which tab 116 is substantially the same as tab 16 shown in FIG. 4, and release means 152 comprises a release strip having a release coated face 156 which is releasably attached to adhesive coating 142 on free end 130 of tab 116. Release strip 152 has a free end 153 which can be conveniently grasped by a user to facilitate in separating release strip 152 from tab 116.

Adhesive tabs suitable for the purposes of the present invention can be made from a wide variety of materials, provided that such materials are sufficiently flexible. Preferred materials for this purpose are polyolefin webs such as polyethylene sheet, polypropylene sheet, and the like. Particularly preferred are webs which are oriented along the narrow dimension of the tab or webs which have filament reinforcements therein and elastic webs which further minimize the stresses transmitted to the diaper backing sheet.

The pressure-sensitive adhesive layers such as adhesive coating 42 are provided by applying a coating of a pressure-sensitive adhesive composition known in the art to the appropriate surface of tab 16. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, and the like.

Anchored release strips can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,800,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, non-woven fabric which is formed, for example, in accordance with the teachings of commonly assigned U.S. Pat. Nos. 2,862,251, 3,081,514 and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd.$^2$.

In addition, facing sheet 20 can be formed of a non-apertured material, such as a nonwoven isotropic web, or the like. In all of the aforementioned facing materials, the material should be relatively hydrophobic so as to retard wicking within the facing layer. Also suitable are porous polymeric sheet materials such as polyalkylene webs having a fibrous surface, and the like.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the tab fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by inserting the corners having tabs 16 through openings 54, pulling free end 30 away from its temporary engagement with release means 52 to expose adhesive coating 42 which was releasably adhered to release means 52. The tabs are then used to secure the diaper in the desired position by simply folding the corners having tabs 16 until backing sheet 24 is juxtaposed to itself, and urging the pressure-sensitive adhesive surfaces in contact with the adjacent outer surface of the diaper. The applied diaper assumes the configuration illustrated in FIG. 2.

The foregoing description and drawing are illustrative but are not to be taken as limiting. Still other variations and modifications are possible without departing from the spirit and scope of the present invention.

I claim:

1. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and an adhesive tab fastener means comprising an integral elongated tape segment having a fixed end permanently attached to a first corner of said diaper along a side margin and one transverse margin of said diaper, and a free working end having a pressure-sensitive adhesive coating on one face thereof, said diaper having an opening at a second corner of said diaper along said side margin and an opposite transverse margin of said diaper, whereby said first corner and said free working end can be inserted through said opening and said free working end can be adhered to said backing sheet to secure said diaper about an infant.

2. The disposable diaper as defined in claim 1 wherein said opening has a length greater than the width of said tape segment.

3. The disposable diaper as defined in claim 1 wherein said first corner is inserted through said opening from said diaper inside surface to said diaper outside surface and is folded back, whereupon said free working end is adhered to said backing sheet.

4. The disposable diaper as defined in claim 3 wherein said free working end is adhered to said backing sheet along said opposite transverse margin of said diaper.

5. The disposable diaper as defined in claim 1 wherein said opening in said diaper extends through only said backing sheet and said facing sheet.

6. The disposable diaper as defined in claim 1 wherein said opening is oblong and is perpendicular to said one transverse margin of said diaper.

7. The disposable diaper as defined in claim 1 wherein release means is releasably attached to said adhesive coating on said free working end, said free end being separable from said release means to make said adhesive-coated free end of said tape segment available for use in securing said diaper about an infant.

* * * * *